US012569302B2

(12) United States Patent
Guthart et al.

(10) Patent No.: US 12,569,302 B2
(45) Date of Patent: Mar. 10, 2026

(54) SURGICAL CLAMP ASSEMBLY FOR FIXING A NAVIGATION TRACKER TO A PORTION OF BONE

(71) Applicant: MAKO Surgical Corp., Weston, FL (US)

(72) Inventors: Matthew Joseph Guthart, Miami, FL (US); Robert Courtney, Jr., Pierceton, IN (US); Andrew Jacob Nelson, New York City, NY (US); Mark Ellsworth Nadzadi, Batavia, OH (US)

(73) Assignee: MAKO Surgical Corp., Weston, FL (US)

( * ) Notice: Subject to any disclaimer, the term of this patent is extended or adjusted under 35 U.S.C. 154(b) by 262 days.

(21) Appl. No.: 18/392,014

(22) Filed: Dec. 21, 2023

(65) Prior Publication Data

US 2024/0206983 A1 Jun. 27, 2024

Related U.S. Application Data

(60) Provisional application No. 63/434,254, filed on Dec. 21, 2022.

(51) Int. Cl.
*A61B 34/20* (2016.01)

(52) U.S. Cl.
CPC ...... *A61B 34/20* (2016.02); *A61B 2034/2046* (2016.02)

(58) Field of Classification Search
CPC .... A61B 2034/2046; A61B 2034/2055; A61B 2090/3983; A61B 2090/3991; A61B 34/20; A61B 34/30; A61B 90/39; A61B 90/05
See application file for complete search history.

(56) References Cited

U.S. PATENT DOCUMENTS 3,746,002 A 7/1973 Haller
3,810,294 A 5/1974 Link
4,744,132 A 5/1988 Greene et al.
(Continued)

FOREIGN PATENT DOCUMENTS

GB 2263432 A 7/1993

OTHER PUBLICATIONS

International Search Report for Application No. PCT/US2023/085388 dated Apr. 30, 2024, 3 pages.
(Continued)

*Primary Examiner* — Scott Luan
(74) *Attorney, Agent, or Firm* — Howard & Howard Attorneys PLLC

(57) ABSTRACT

A surgical clamp assembly for clamping tissue and supporting a navigation tracker. The assembly includes a clamp body. Clamp arms are coupled to the clamp body to grip tissue. At least one of the clamp arms includes a distal portion having a clamp surface to grip tissue and a proximal portion that is pivotable relative to the clamp body about a first pivot. A linear displacement mechanism and a carrier are coupled to the clamp body. The carrier is moveable relative to the clamp body along a carrier axis in response to movement of the linear displacement mechanism. The carrier is coupled directly to the proximal portion of the clamp arm. The clamp arm is also pivotable relative to the carrier about a second pivot in response to movement of the carrier.

19 Claims, 6 Drawing Sheets

(56) References Cited

U.S. PATENT DOCUMENTS

| | | | |
|---|---|---|---|
| 5,417,693 | A | 5/1995 | Sowden et al. |
| 5,732,992 | A | 3/1998 | Mauldin |
| 5,944,723 | A | 8/1999 | Colleran et al. |
| 6,226,548 | B1 | 5/2001 | Foley et al. |
| 6,719,757 | B2 | 4/2004 | Neubauer et al. |
| 6,942,676 | B2 | 9/2005 | Buelna |
| 7,107,091 | B2 | 9/2006 | Jutras et al. |
| 7,669,306 | B2 | 3/2010 | Palka |
| 7,699,847 | B2 | 4/2010 | Sheldon et al. |
| 7,727,237 | B2 | 6/2010 | Birkbeck et al. |
| 7,993,353 | B2 | 8/2011 | Roeßner et al. |
| 8,002,772 | B2 | 8/2011 | Sarin et al. |
| 8,114,085 | B2 | 2/2012 | von Jako |
| 8,192,449 | B2 | 6/2012 | Maier et al. |
| 8,475,470 | B2 | 7/2013 | von Jako |
| 8,535,329 | B2 | 9/2013 | Sarin et al. |
| 8,715,296 | B2 | 5/2014 | Plassky et al. |
| 8,939,995 | B2 | 1/2015 | Lechner et al. |
| 8,979,852 | B2 | 3/2015 | Taber et al. |
| 9,008,757 | B2 | 4/2015 | Wu |
| 9,011,441 | B2 | 4/2015 | Bertagnoli et al. |
| 9,072,522 | B2 | 7/2015 | Morejohn et al. |
| 9,101,412 | B2 | 8/2015 | Bootwala et al. |
| 9,119,655 | B2 | 9/2015 | Bowling et al. |
| 9,566,121 | B2 | 2/2017 | Staunton et al. |
| 9,603,665 | B2 | 3/2017 | Bowling et al. |
| 9,775,650 | B2 | 10/2017 | Buttermann |
| 9,855,065 | B2 | 1/2018 | Wyant et al. |
| 9,937,058 | B2 | 4/2018 | Axelson, Jr. et al. |
| 9,951,904 | B2 | 4/2018 | Perez et al. |
| 9,993,273 | B2 | 6/2018 | Moctezuma de la Barrera et al. |
| 10,098,672 | B2 | 10/2018 | Moskowitz et al. |
| 10,314,599 | B2 | 6/2019 | Hampp et al. |
| 10,441,365 | B2 | 10/2019 | McLachlin et al. |
| 10,463,434 | B2 | 11/2019 | Siegler et al. |
| 10,537,395 | B2 | 1/2020 | Perez |
| 10,835,296 | B2 | 11/2020 | Elimelech et al. |
| 11,389,252 | B2 | 7/2022 | Gera et al. |
| 11,432,945 | B2 | 9/2022 | Viscardi et al. |
| 12,108,973 | B2 | 10/2024 | López Del Pueyo et al. |
| 2004/0068263 | A1 | 4/2004 | Chouinard et al. |
| 2005/0113677 | A1 | 5/2005 | Davies et al. |
| 2005/0149050 | A1 | 7/2005 | Stifter et al. |
| 2005/0267480 | A1 | 12/2005 | Suddaby |
| 2007/0276370 | A1 | 11/2007 | Altarac et al. |
| 2008/0103512 | A1 | 5/2008 | Gately |
| 2009/0062869 | A1* | 3/2009 | Claverie ........... A61B 17/8866 |
| | | | 606/151 |
| 2009/0240280 | A1 | 9/2009 | Wang et al. |
| 2009/0306499 | A1 | 12/2009 | Van Vorhis et al. |
| 2010/0207385 | A1 | 8/2010 | Nishimura |
| 2011/0004259 | A1 | 1/2011 | Stallings et al. |
| 2013/0113150 | A1 | 5/2013 | Velez |
| 2015/0282735 | A1 | 10/2015 | Rossner |
| 2017/0281202 | A1 | 10/2017 | Hampp et al. |
| 2018/0110572 | A1 | 4/2018 | Flatt |
| 2018/0177557 | A1 | 6/2018 | Kapadia et al. |
| 2022/0125496 | A1 | 4/2022 | López Del Pueyo et al. |
| 2022/0257334 | A1 | 8/2022 | Guthart et al. |
| 2023/0094132 | A1 | 3/2023 | Basta et al. |
| 2024/0225473 | A1 | 7/2024 | Reddy et al. |

OTHER PUBLICATIONS

Amazon, "Higatful Super Clamp, Camera Clamp Mount with Locating Pin for ARRI Standard, 1/4"-20 & 3/8-16 Thread Versatile Strong C Clamp Accessories Compatible with Gopro/Monitor/LED Lights/Flash/Microphone", https://www.amazon.com.au/Locating-Versatile-Accessories-compatible-Microphone/dp/B09TXDBDYX, 1996-2024, 4 pages.

* cited by examiner

SURGICAL CLAMP ASSEMBLY FOR FIXING A NAVIGATION TRACKER TO A PORTION OF BONE

CROSS-REFERENCE TO RELATED APPLICATIONS

The subject patent application claims priority to and all the benefits of U.S. Provisional Patent App. No. 63/434,254, filed Dec. 21, 2022, the entire contents of which are hereby incorporated by reference.

BACKGROUND

Surgical navigation systems assist users in locating surgical objects in the operating room. The navigation system includes a localizer that can use any type of sensing modality to determine the position and/or orientation of tracking devices attached to the surgical objects. The surgical objects are often instruments, devices, or an anatomic object, such as bone.

Attaching the tracking device to a bone has historically required securing a screw, plate, or other fastener to the bone to provide a rigid frame for the tracking device relative to the bone. However, such fastening techniques are undesirable as they require invasively drilling fasteners into the bone. Moreover, because these fastening techniques require drilling into the bone, the surgeon is often prevented from easily adjusting the setup of the tracking device. For example, the surgeon may need to relocate the tracking device due to the size of the patient or incision at the surgical site, etc.

Other attachment mechanisms have included clamps that secure to the bone.

However, conventional bone clamps have been limited in the amount of force they can exert on the bone. In turn, the lack of clamping force may comprise the rigid connection to the bone and cause loss of tracking accuracy or loss of tracking altogether. Furthermore, certain procedures, like joint arthroplasty, involve long bones, such as the femur and humerus, which significantly vary in size from patient to patient. Yet, the range of motion of the jaws of a conventional bone clamp is limited. In turn, the reduced range of motion limits the size of bones that can fit between the jaws of the conventional bone clamp. Additionally, conventional bone clamps present a relatively large footprint, which may not be conducive for procedures having limited access angle or incision size. Moreover, the mechanisms or techniques involved with closing and opening the jaws of conventional bone clamps are often not ergonomic or user friendly and may increase the risk of collisions at the surgical site.

SUMMARY

This Summary introduces a selection of concepts in a simplified form that are further described below in the Detailed Description. This Summary is not intended to limit the scope of the claimed subject matter nor identify key features or essential features of the claimed subject matter.

According to a first aspect, a surgical clamp assembly for clamping tissue and supporting a navigation tracker is provided. The surgical clamp assembly comprises a clamp body. A first clamp arm is coupled to the clamp body. A second clamp arm is coupled to the clamp body and configured to grip tissue with the first clamp arm. The second clamp arm comprises a distal portion having a clamp surface. The second clamp arm comprises a proximal portion pivotable relative to the clamp body about a first pivot. A linear displacement mechanism is coupled to the clamp body. A carrier is coupled to the linear displacement mechanism. The carrier is moveable relative to the clamp body along a carrier axis in response to movement of the linear displacement mechanism. The carrier is coupled directly to the proximal portion of the second clamp arm. The proximal portion of the second clamp arm is pivotable relative to the carrier about a second pivot in response to movement of the carrier.

According to a second aspect, a surgical attachment system for fixing a navigation tracker to a portion of bone is provided. The surgical attachment system comprises an extension arm configured to support the navigation tracker. The surgical attachment system further comprises a surgical clamp assembly configured to support the extension arm. The surgical clamp assembly comprises a clamp body. A first clamp arm is coupled to the clamp body. A second clamp arm is coupled to the clamp body and configured to grip tissue with the first clamp arm. The second clamp arm comprises a distal portion having a clamp surface. The second clamp arm comprises a proximal portion pivotable relative to the clamp body about a first pivot. A linear displacement mechanism is coupled to the clamp body. A carrier is coupled to the linear displacement mechanism. The carrier is moveable relative to the clamp body along a carrier axis in response to movement of the linear displacement mechanism. The carrier is coupled directly to the proximal portion of the second clamp arm. The proximal portion of the second clamp arm is pivotable relative to the carrier about a second pivot in response to movement of the carrier.

According to a third aspect, a surgical tracking system is provided. The surgical tracking system comprises a navigation tracker. The surgical tracking system further comprises a surgical attachment system for fixing the navigation tracker to a portion of bone. The surgical attachment system comprises an extension arm configured to support the navigation tracker. The surgical attachment system further comprises a surgical clamp assembly configured to support the extension arm. The surgical clamp assembly comprises a clamp body. A first clamp arm is coupled to the clamp body. A second clamp arm is coupled to the clamp body and configured to grip tissue with the first clamp arm. The second clamp arm comprises a distal portion having a clamp surface. The second clamp arm comprises a proximal portion pivotable relative to the clamp body about a first pivot. A linear displacement mechanism is coupled to the clamp body. A carrier is coupled to the linear displacement mechanism. The carrier is moveable relative to the clamp body along a carrier axis in response to movement of the linear displacement mechanism. The carrier is coupled directly to the proximal portion of the second clamp arm. The proximal portion of the second clamp arm is pivotable relative to the carrier about a second pivot in response to movement of the carrier.

According to a fourth aspect, a navigation system is provided which includes a localizer for tracking the navigation tracker attached to the surgical attachment system of the third aspect.

Any of the above aspects can be utilized individually, or in combination.

Any of the above aspects can be utilized with any of the following implementations:

In one implementation the first pivot is fixed relative to the clamp body and the proximal portion of the second clamp arm such that the second clamp arm is pivotable relative to the clamp body. In one implementation the second pivot is fixed relative to the proximal portion of the second clamp arm and moveable relative to the carrier such that the second clamp arm is pivotable and translatable relative to the carrier.

In one implementation a retainer is disposed at the second pivot and the retainer is coupled to the proximal portion of the second clamp arm and the carrier and the carrier defines a slot to receive the retainer. In one implementation the slot is sized to permit the retainer to rotate and translate within the slot. In one implementation the slot is sized to permit the retainer to move along a respective slot axis that is perpendicular to the carrier axis. In one implementation the carrier comprises opposing slot walls of the slot that defines a height of the slot and the carrier comprises opposing slot ends defining a width of the slot and the height of the slot approximates a height of the retainer. In one implementation the width of the slot is greater than the height of the slot.

In one implementation the linear displacement mechanism comprises a linearly translatable lead screw. In one implementation the second clamp arm comprises an arm grip on the clamp surface and the clamp body comprises a body grip and the arm grip and the body grip are configured to grip tissue. In one implementation the clamp body comprises a stationary portion that remains stationary while the second clamp arm moves about the first pivot and the stationary portion comprises a distal-facing surface and a grip extending distally from the distal-facing surface. In one implementation the grip and the stationary portion of the clamp body are monolithic in construction.

In one implementation the linear displacement mechanism is engageable with the carrier such that the carrier is moveable along the carrier axis in response to rotation of the linear displacement mechanism. In one implementation the linear displacement mechanism is threadably engageable with the carrier. In one implementation the clamp body defines a channel to receive the carrier and permit the carrier to move along the carrier axis. In one implementation the carrier axis is centered in the channel. In one implementation the clamp body defines a notch further defining the channel and the notch is configured to at least partially receive the second clamp arm to permit the second clamp arm to pivot about the first pivot with a greater range.

In one implementation the clamp body comprises an attachment interface for detachable coupling to an extension arm. In one implementation the attachment interface is oriented transverse to the carrier axis. In one implementation the first pivot is disposed at a first distance from the carrier axis and the second pivot is disposed at a second distance from the carrier axis less than the first distance. In one implementation the first clamp arm is fixed to the clamp body. In one implementation the first clamp arm is pivotable relative to the clamp body and the carrier and configured to move in concert with the second clamp arm. In one implementation the first clamp arm is symmetrical of the second clamp arm about a reference plane extending through the carrier axis. In one implementation, the clamp body is integrally coupled to the extension arm.

In one implementation a connector is coupled to the extension arm for coupling to the navigation tracker and first and second tracker rotational adjusters disposed between the extension arm and the connector and the first tracker rotational adjuster is configured to selectively rotate the connector relative to the first end of the extension arm about a first connector axis and the second tracker rotational adjuster is configured to selectively rotate the connector about a second connector axis perpendicular to the first connector axis.

In one implementation the first and second tracker rotational adjusters each comprise a pair of opposing lock teeth, with the pair of opposing lock teeth configured to rotate relative to one another when spaced apart and rotatably lock when in engagement with one another. In one implementation an extension arm rotational adjuster is configured to selectively rotate the second end of the extension arm relative to the clamp body about an arm axis. In one implementation arm axis is transverse to the carrier axis. In one implementation the extension arm rotational adjuster and the clamp body each comprise lock teeth opposing each other and the lock teeth on the extension arm rotational adjuster and the lock teeth on the clamp body are configured to rotate relative to each other when spaced apart and rotatably lock when in engagement with each other. In one implementation, the tissue is a bone, such as a long bone, including but not limited to a femur, tibia, or humerus.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Example Surgical System

Referring to the Figures, wherein like numerals indicate like or corresponding parts throughout the several views, an example of a surgical system 10 (hereinafter "system") is shown throughout.

Figure 1:
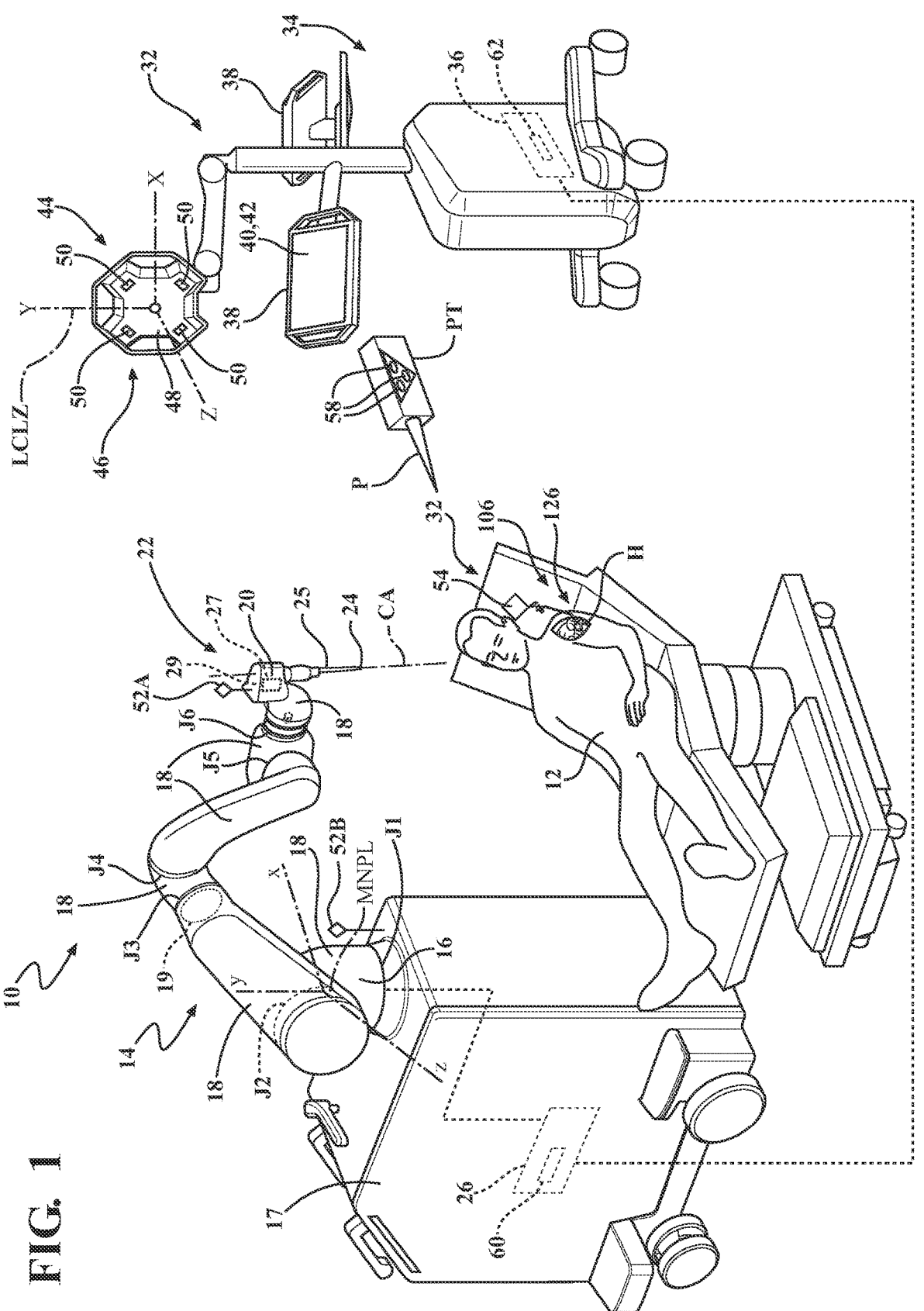
FIG. 1 is a perspective view of a robotic system for manipulating a target tissue of a patient with a tool, according to one example, including a surgical navigation system having a surgical attachment system and a navigation tracker.

As shown in FIG. 1, the system 10 may treat an anatomy (surgical site) of a patient 12, such as bone or soft tissue. In FIG. 1, the patient 12 is undergoing a surgical procedure. The anatomy in FIG. 1 includes a humerus (H) of the patient 12. The surgical procedure may involve tissue removal or treatment. Treatment may include cutting, coagulating, lesioning the tissue, treatment in place of tissue, or the like. In one example, the surgical procedure is a shoulder joint procedure, such as reverse shoulder arthroplasty, anatomical shoulder arthroplasty, shoulder revision surgery, or the like. Alternatively, the surgical procedure may be a partial or total knee or hip replacement surgery. In one example, the system 10 is designed to cut away material to be replaced by surgical implants, such as glenoid implants, humeral implants, hip and knee implants, including unicompartmental, bicompartmental, multicompartmental, or total knee implants. The implants used with the techniques described here can be like that disclosed in U.S. Pat. No. 9,937,058, entitled, "Prosthetic Implant and Method of Implantation," and U.S. Pat. No. 11,432,945, entitled "Robotic System For Shoulder Arthroplasty Using Stemless Implant Components", the entire disclosure of each of these patents being hereby incorporated by reference. The system 10 disclosed herein may be used to perform other procedures, surgical or non-surgical, or may be used in industrial applications or other applications where robotic systems are utilized.

The system 10 may include a robotic manipulator 14. The robotic manipulator 14 has a base 16 and plurality of links 18. A manipulator cart 17 supports the robotic manipulator 14 such that the robotic manipulator 14 is fixed to the manipulator cart 17. The links 18 collectively form one or more arms of the robotic manipulator 14. The robotic manipulator 14 may have a serial arm configuration (as shown in FIG. 1) or a parallel arm configuration. In other examples, more than one robotic manipulator 14 may be utilized in a multiple arm configuration. The robotic manipulator 14 may comprise a plurality of (prismatic and/or rotating) joints (J) and a plurality of motor and/or joint encoders 19 located at the joints (J) for determining position data of the joints (J). For simplicity, only one joint encoder 19 is illustrated in FIG. 1, although it is to be appreciated that the other joint encoders 19 may be similarly illustrated. The robotic manipulator 14 according to one example has six joints (J1-J6) implementing at least six-degrees of freedom (DOF) for the robotic manipulator 14. However, the robotic manipulator 14 may have any number of degrees of freedom and may have any suitable number of joints (J) and redundant joints (J).

A surgical tool 20 (hereinafter "tool") couples to the robotic manipulator 14 and is movable relative to the base 16 to interact with the anatomy in certain modes. The tool 20 is or can form part of an end effector 22. The tool 20 may be grasped by the operator. One exemplary arrangement of the robotic manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The robotic manipulator 14 and the tool 20 may be arranged in alternative configurations. The tool 20 can be like that shown in U.S. Pat. No. 9,566,121, filed on Mar. 15, 2014, entitled, "End Effector of a Surgical Robotic Manipulator," hereby incorporated by reference.

The positioning of the end effector 22 and the tool 20 is defined by the robotic manipulator 14. The tool 20 includes an energy applicator 24 designed to contact the target site, such as the tissue of the patient 12 at the surgical site. The energy applicator 24 may be a drill, a saw blade, a bur, an ultrasonic vibrating tip, or the like.

The system 10 includes a controller 30. The controller 30 includes software and/or hardware for controlling the robotic manipulator 14. The controller 30 directs the motion of the robotic manipulator 14 and controls a state (position and/or orientation) of the tool 20 with respect to a coordinate system of the manipulator 14.

As shown in FIG. 1, the system 10 further includes a surgical navigation system 32. The navigation system 32 may be utilized with any surgical setup and is not required to be utilized with the robotic manipulator 14. The surgical navigation system 32 is configured to track movement of various objects. Such objects include, for example, the robotic manipulator 14, the tool 20, or any other surgical tool, such as a probe, and the anatomy, e.g., humerus H.

The surgical navigation system 32 may include a cart assembly 34 that houses a navigation computer 36, and/or other types of control units. A navigation interface may be in operative communication with the navigation computer 36. The navigation interface includes one or more displays 38. First and second input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The surgical navigation system 32 also includes a navigation localizer 44 (hereinafter "localizer") coupled to the navigation computer 36. The surgical navigation system 32 utilizes the localizer 44 to track surgical objects and gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein.

In one example, the localizer 44 is an optical localizer and includes a camera unit 46. The camera unit 46 has an outer casing 48 that houses one or more optical sensors 50.

The surgical navigation system 32 may include one or more trackers. In one example, the trackers include a pointer tracker PT, one or more manipulator trackers 52, and one or more patient trackers 54. In the illustrated example of FIG. 1, the pointer tracker PT is firmly affixed to a pointer P used for registering the anatomy to the localizer coordinate system LCLZ. A manipulator tracker 52 is firmly attached to the tool 20 (i.e., tracker 52A). The manipulator tracker 52 may be affixed to any suitable component of the robotic manipulator 14, in addition to, or other than the tool 20, such as the base 16 (i.e., tracker 52B), or any one or more links 18 of the robotic manipulator 14. In the example shown, the patient tracker 54 is firmly affixed to a bone, such as the humerus H of the patient 12. Of course, depending on the procedure, the patient tracker 54 could alternatively be affixed to any other type of anatomy or bone. Additionally, the tracker 54 may be affixed on left or right sides of the patient anatomy. Systems, assemblies, and techniques involving securing the patient tracker to the anatomy are described in the section below.

Any one or more of the trackers may include active markers 58. The active markers 58 may include light emitting diodes (LEDs). Alternatively, the trackers 52, 54 may have passive markers, such as reflectors, which reflect light emitted from the camera unit 46. Other suitable markers not specifically described herein may be utilized.

The localizer 44 tracks the trackers 52, 54 to determine a state of each of the trackers 52, 54 which correspond respectively to the state of the object respectively attached thereto. The localizer 44 provides the state of the trackers 52, 54 to the navigation computer 36. In one example, the navigation computer 36 determines and communicates the state the trackers 52, 54 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the surgical navigation system 32 is shown in the Figures, the surgical navigation system 32 may have any other suitable configuration for tracking the robotic manipulator 14 and the patient 12. In one example, the surgical navigation system 32 and/or localizer 44 are ultrasound-based. In another example, the surgical navigation system 32 and/or localizer 44 are radio frequency (RF)-based. In another example, the surgical navigation system 32 and/or localizer 44 are machine-vision based. The navigation system 32 can utilized any combination of these modalities. The surgical navigation system 32 can include any aspects of the navigation systems described in U.S. Pat. No. 9,008,757 entitled, "Navigation System Including Optical and Non-Optical Sensors," or U.S. Pat. No. 9,603,665 entitled "System And Methods For Establishing Virtual Constraint Boundaries", the entire contents of each of these patents being hereby incorporated by reference.

The surgical navigation system 32 and/or localizer 44 may have any other suitable components or structure not specifically recited herein. Furthermore, any of the techniques, methods, and/or components described above with respect to the camera-based surgical navigation system 32 shown throughout the Figures may be implemented or provided for any of the other examples of the surgical navigation system 32 described herein. For example, the surgical navigation system 32 may utilize solely inertial tracking or any combination of tracking techniques.

The controller 30 further includes software modules. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the robotic manipulator 14. In one example, as shown in FIG. 1, the manipulator controller is implemented on the manipulator computer 26. The manipulator controller 60 may receive and process data from a single source or multiple sources. The controller 30 further includes a navigation controller 62 for communicating the state data relating to the bone, e.g., humerus H or scapula, and robotic manipulator 14 to the manipulator controller 60. The manipulator controller 60 receives and processes the state data provided by the navigation controller 62 to direct movement of the robotic manipulator 14. In one example, as shown in FIG. 1, the navigation controller 62 is implemented on the navigation computer 36. The manipulator controller 60 or navigation controller 62 may also communicate states of the patient 12 and robotic manipulator 14 to the operator by displaying an image of the humerus H and/or scapula and the robotic manipulator 14 on the one or more displays 38. The manipulator computer 26 or navigation computer 36 may also command display of instructions or request information using the display 38 to interact with the operator and for directing the robotic manipulator 14.

The robotic system shown in FIG. 1 is provided only as one possible example of a system that can be utilized with the clamping and attachment system described in the next section. The clamping and attachment system can be utilized with any type of navigated surgical system, such as one including manual hand-held tools, robotic hand-held tools, imaging systems (e.g., CT, X-ray, C-arms, etc.), or and for any type of navigated orthopedic or non-orthopedic procedure.

II. Surgical Clamping and Attachment System

Described in this section are surgical clamping and attachment systems that can be utilized with a navigation tracker 54, such as that shown in FIG. 1. The navigation tracker 54 is utilized as the patient tracker described above, with the navigation computer 36 determining the state of the navigation tracker 54 to track the patient 12. The navigation tracker 54 can have various configurations depending on the tracking modalities described above.

Figure 2:
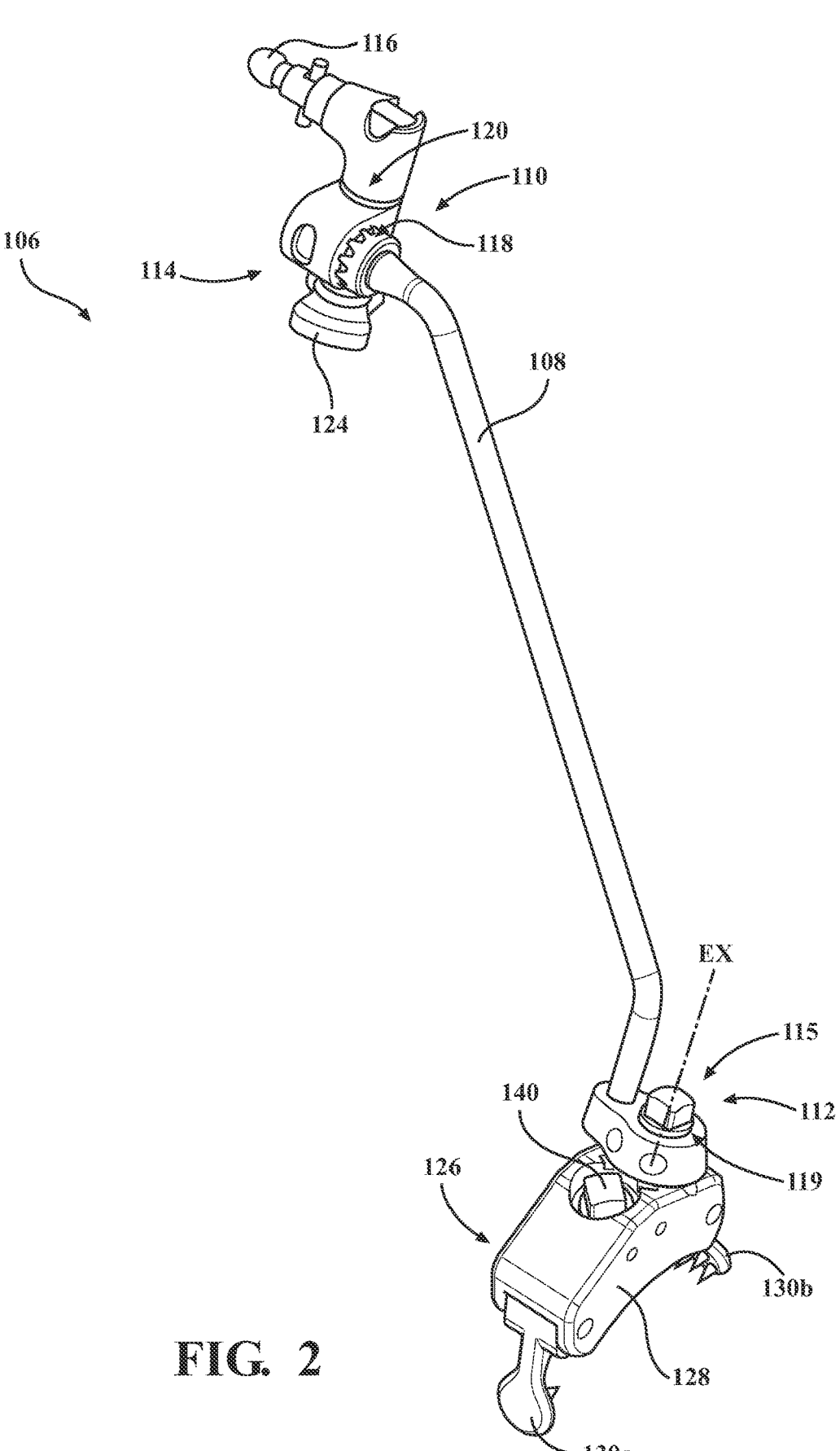
FIG. 2 is a perspective view of the surgical attachment system of FIG. 1.

As shown in FIG. 2, the surgical navigation system 32 further comprises a surgical attachment system 106 for fixing the navigation tracker 54 to a portion of bone. As will become apparent from description below, the surgical attachment system 106 is configured to be selectively connected to and disconnected from the bone. In one example, the bone is the humerus H subject to a shoulder surgery. However, the surgical attachment system 106 may be configured to be fixed to any suitable bone, such as a scapula, femur, tibia, pelvis, or any part of the spinal bone (vertebra or spinous process).

The surgical attachment system 106 may include an extension arm 108 with a first end 110 and a second end 112. The extension arm 108 may have a substantially cylindrical configuration. In other configurations, the extension arm 108 may be configured as a bent rod or a curved cylinder. However, the extension arm 108 may have any suitable configuration for supporting the navigation tracker 54 at a position spaced from the patient 12. The extension arm 108 can have any suitable length to enable the navigation tracker 54 to be exposed relative to the surgical site, and hence, trackable by the navigation system 32. One example of an extension arm 108 that can be utilized with the navigation system 32 and other portions of the attachment system 106 is disclosed in commonly owned U.S. patent application Ser. No. 17,673,055, published as U.S. Patent Publication No. 2022/0257334, entitled "Clamp Assembly for Fixing a Navigation Tracker to a Portion of Bone" the entire disclosure of which is hereby incorporated by reference.

The attachment system 106 may comprise a first extension attachment interface 114 disposed at the first end 110 of the extension arm 108. The first extension attachment interface 114 may be configured to detachably couple to the navigation tracker 54. In other configurations, the extension arm 108 may be coupled to the navigation tracker 54 such that the extension arm 108 and the navigation tracker 54 are not detachable. In other words, the extension arm 108 may be rigidly attached to the navigation tracker 54. In such a configuration, the extension arm 108 may still be configured to be selectively rotatably relative to the navigation tracker 54. In still other configurations, the extension arm 108 may be integral with the navigation tracker 54. A second extension attachment interface 115 may be disposed at the second end 112 of the extension arm 108. The second extension attachment interface 115 may be configured for detachable coupling to a clamp assembly 126, as described in greater detail below. The first extension attachment interface 114 may comprise a connector 116 for coupling to the navigation tracker 54 and first and second tracker rotational adjusters 118, 120 disposed between the extension arm 108 and the connector 116.

The connector 116 may be configured as a quick-connect coupler. More specifically, the quick-connect coupler corresponds with a connector on the navigation tracker 54. Coupling the navigation tracker 54 to the quick-connect coupler may be performed by pushing the connector of the navigation tracker 54 onto the quick-connect coupler until the connector no longer moves on the quick-connector coupler. The connector on the navigation tracker 54 may be actuated (e.g., by sliding a collar) to remove the navigation tracker 54 from the first extension attachment interface 114. Although the connector 116 of the first extension attachment interface 114 is shown as a quick-connect coupler, the connector 116 may be configured in any other suitable configuration for coupling the navigation tracker 54 to the first extension attachment interface (e.g., threaded engagement). The connector 116 may provide a kinematic coupling to the navigation tracker 54. One example of such quick-connect couplers for a navigation tracker 54 is disclosed in U.S. Pat. No. 10,537,395, entitled "Navigation Tracker with Kinematic Connector Assembly" the entire disclosure of which is hereby incorporated by reference.

The first tracker rotational adjuster 118 may be configured to selectively rotate the connector 116 relative to the first end 110 of the extension arm 108 about a first connector axis. The second tracker rotational adjuster 112 may be configured to selectively rotate the connector 116 about a second connector axis that is perpendicular to the first connector axis. Said differently, the first and second tracker rotational adjusters 118, 120 enable the selective adjustment of the navigation tracker 54 about two degrees of freedom. Furthermore, the first and second tracker rotational adjusters 118, 120 are configured to selectively maintain the navigation tracker 54 in a desired position for allowing the navigation computer 36 to determine and communicate the state of the navigation tracker 54 to the manipulator computer 26 (i.e., by locking the first and second rotational adjusters 118, 120 and preventing rotation about the arm and connector axes).

The first and second tracker rotational adjusters 118, 120 may each comprise a pair of opposing lock teeth, with the pair of opposing lock teeth configured to rotate relative to one another when spaced apart and rotatably lock when in engagement with one another. The first extension attachment interface 114 may further comprise a knob 124. The knob 124 may be operably coupled to each of the first and second rotational adjusters 118, 120. More specifically, rotating the knob 124 may change the spacing between the opposing lock teeth. For example, rotating the knob 124 in a counterclockwise direction (i.e., loosening the knob) moves apart the opposing lock teeth of each of the first and second rotational adjusters 118, 120. When the opposing lock teeth are spaced sufficiently apart, the teeth may rotate relative to one another about the respective arm and connector axes thus allowing the rotation of the first and second rotational adjusters 118, 120 about the axes. On the other hand, rotating the knob 124 in a clockwise direction (i.e., tightening the knob) may move together the opposing lock teeth of each of the first and second tracker rotational adjusters. When the opposing lock teeth contact one another (with opposing lock teeth alternating side-by-side about the respective arm and connector axes), the teeth may not rotate relative to one another about respective arm and connector axes thus locking rotation of the first and second tracker rotational adjusters 118, 120 about the connector axes.

The second extension attachment interface 115 may comprise an extension arm rotational adjuster 119 similar to the tracker rotational adjusters 118, 120. The extension arm rotational adjuster 119 may be configured to selectively rotate the second end 112 of the extension arm 108 relative to a clamp body 128 of the clamp assembly 126 about an arm axis EX. The extension arm rotational adjuster 119 may be configured to be threadably coupled to the clamp body 126 to secure the extension arm 108 to the clamp assembly 126. The extension arm rotation adjuster 119 may be configured to be rotated by a powered hand tool or a non-powered (manually driven) hand tool. In another configuration, the extension arm rotational adjuster 119 may comprise a knob, dial, or other similar shape to be graspable by a user and facilitate coupling. Other couplers are contemplated. For instance, the extension arm rotational adjuster 119 may comprise a post that is received by the clamp body 126 and a clamp (not shown) may be manipulated by the user to secure the post to the clamp body 126.

One example of the first and second extension attachment interfaces 114, 115 are shown in the Figures. However, the first and second extension attachment interfaces 114, 115 may utilize any suitable configuration for allowing selective rotation of the navigation interface about the connector axes and the extension arm 108 about the arm axis EX.

In other configurations, the extension arm 108 may be coupled to the clamp body 126 of the clamp assembly 112 such that the extension arm 108 and the clamp body 126 are not detachable. In other words, the extension arm 108 may be rigidly attached to the navigation tracker clamp body 126. In such a configuration, the extension arm 108 may still be configured to be selectively rotatably relative to the clamp body 126. In still other configurations, the extension arm 108 may be integral with the clamp body 126.

Figures 3, 4:
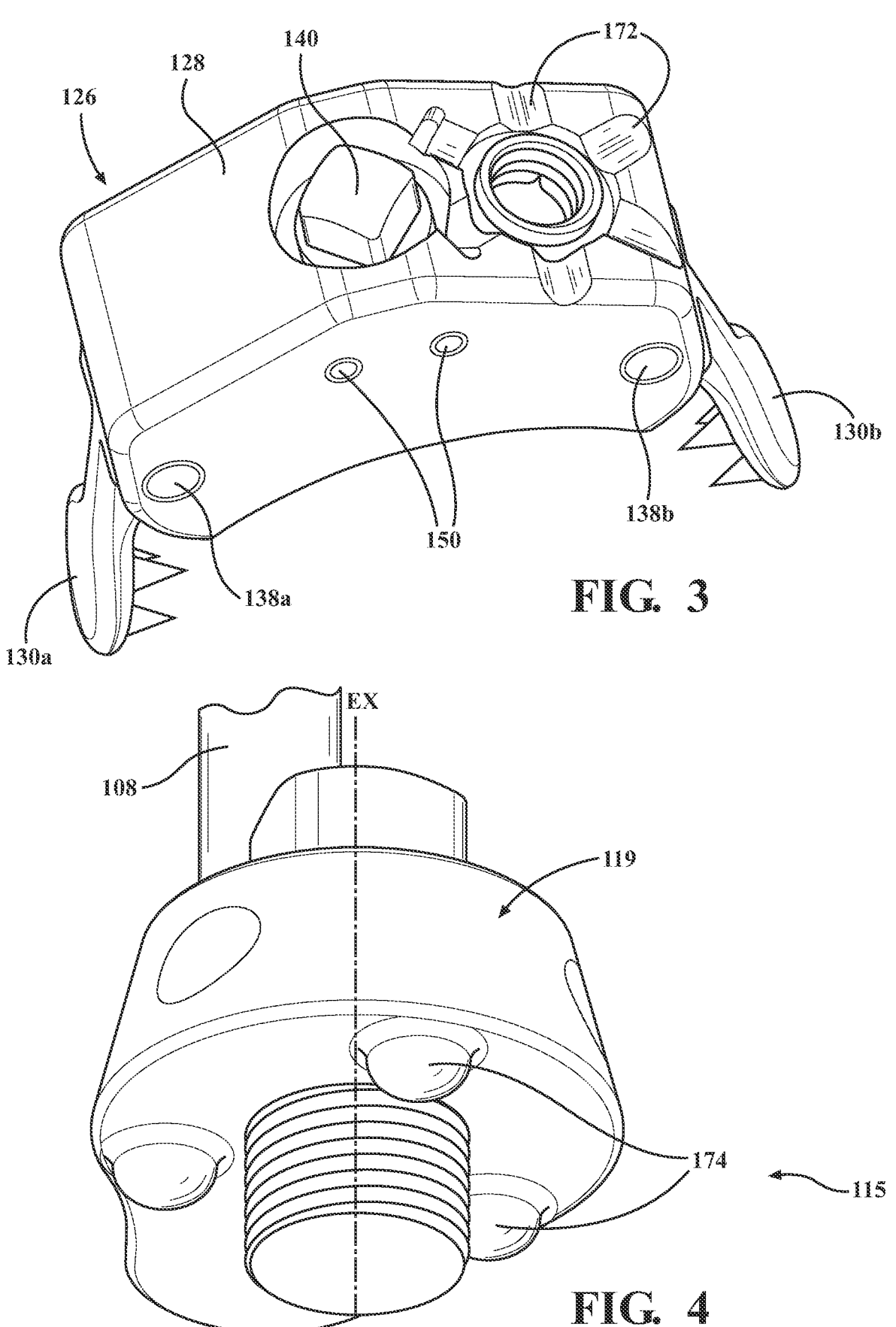
FIG. 3 is a perspective view of a surgical clamp assembly of the surgical attachment system of FIG. 1.
FIG. 4 is a perspective view of an attachment interface of an extension arm of the surgical attachment system of FIG. 1.

As shown in FIGS. 1 and 3, the surgical attachment system 106 includes a surgical clamp assembly 126 disposed at the second end 112 of the extension arm 108 for clamping tissue and fixing the navigation tracker 54 to the portion of the bone. The surgical clamp assembly 126 includes a clamp body 128. First and second clamp arms 130a, 130b are coupled to the clamp body 128 and configured to grip tissue adjacent the clamp body 128. In some configurations, one of the first and second clamp arms 130a, 130b is fixed to the clamp body 128. In such a configuration, the fixed clamp arm and the clamp body 128 may comprise a single body such that the clamp body 128 and the fixed clamp arm are monolithic in construction. In another configuration, one of the clamp arms 130a, 130b may be coupled to the clamp body 128 in any suitable manner, including welding, chemical adhesion, and mechanical fastening. In still other configurations, both the first and second clamp arms 130, 132 are pivotably coupled to the clamp body 128.

Figure 5:
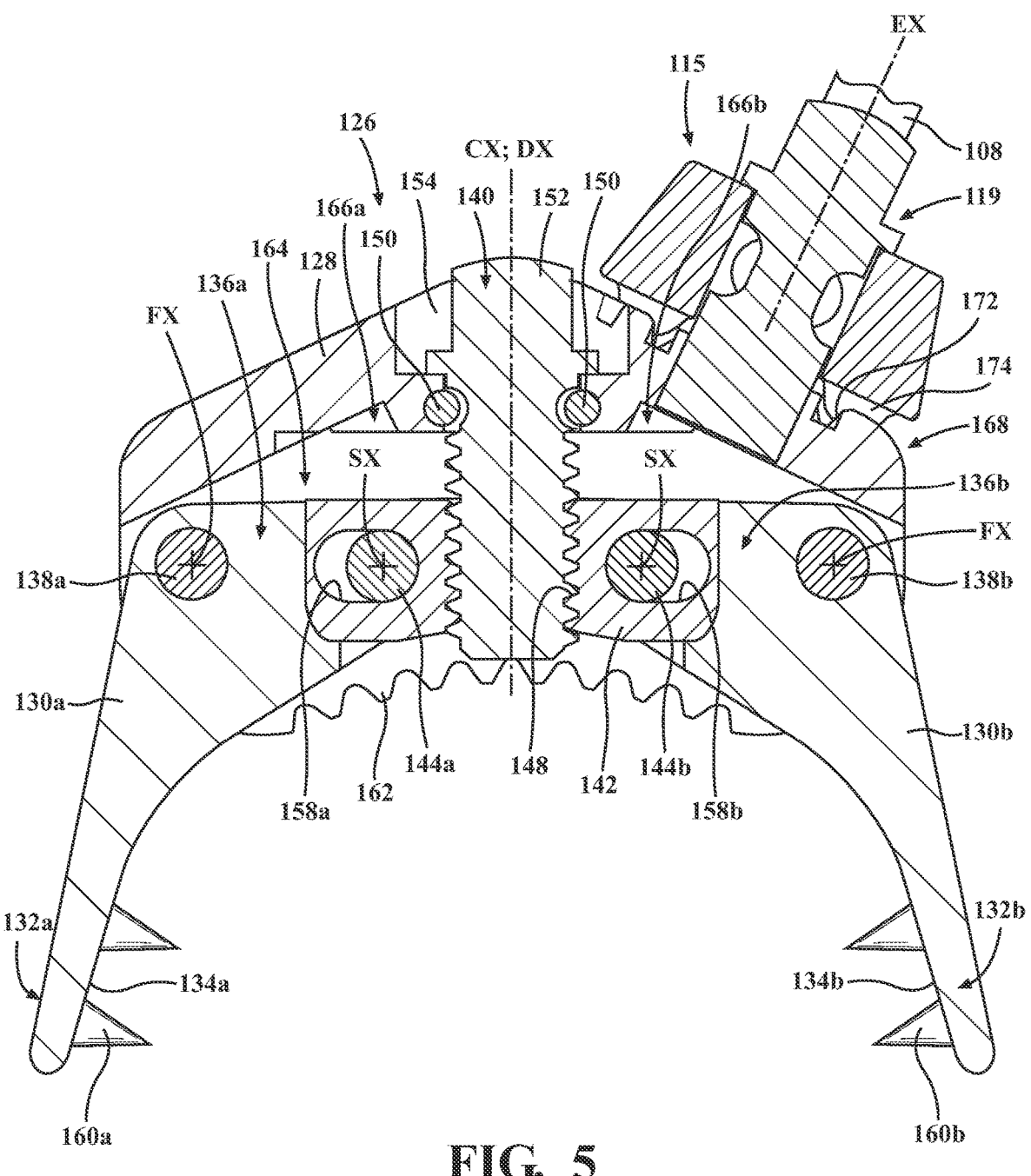
FIG. 5 is a sectional view of the surgical clamp assembly of FIG. 3 in a first configuration.
Figure 6:
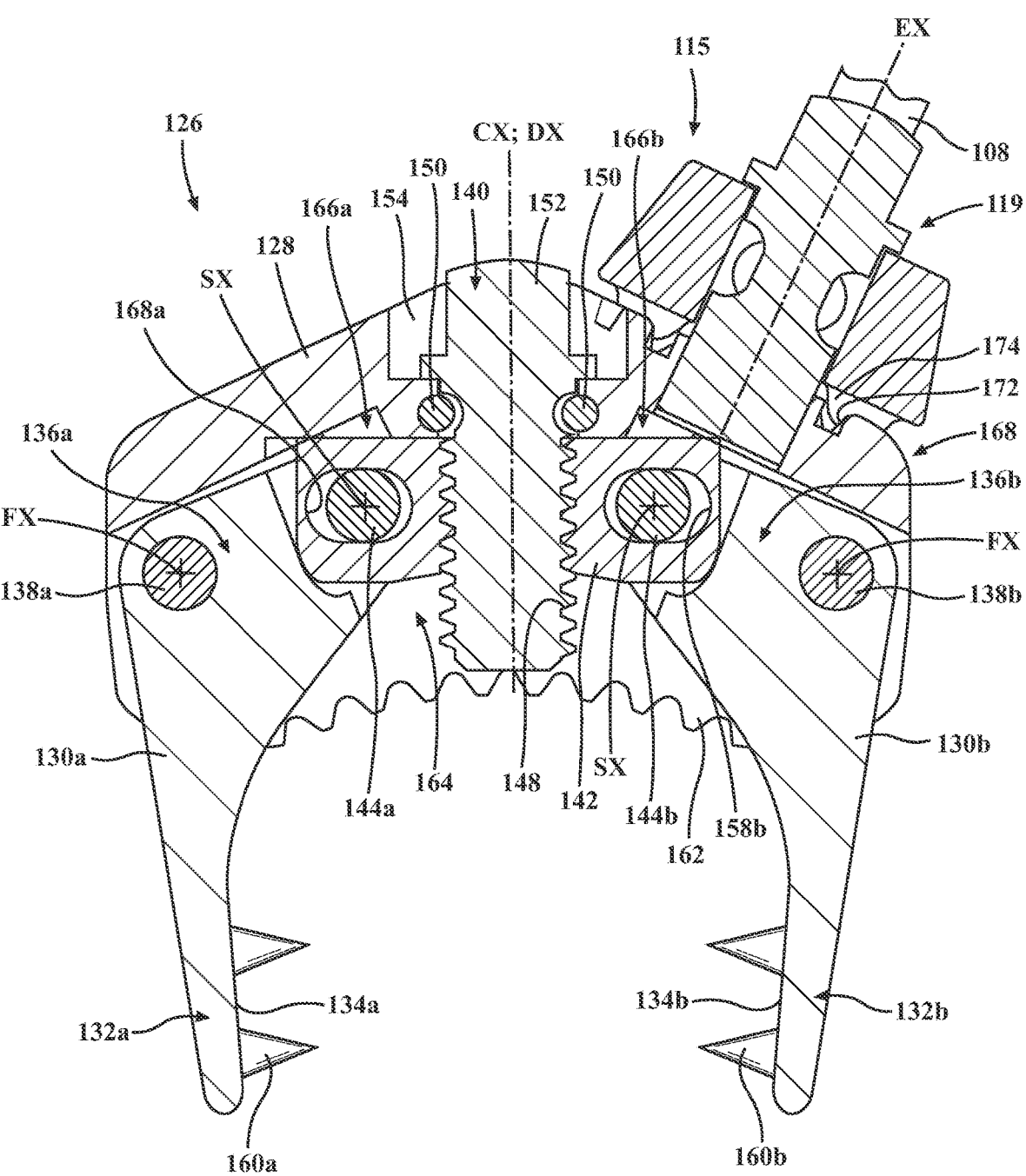
FIG. 6 is a sectional view of the surgical clamp assembly of FIG. 3 in a second configuration.

As shown in the example of FIGS. 5 and 6, the first and second clamp arms 130a, 130b are each pivotably coupled to the clamp body 128. The clamp arms 130a, 130b may each include a distal portion 132a, 132b having a clamp surface 134a, 134b and a proximal portion 136a, 136b that is pivotable relative to the clamp body 128 about a first pivot 138a, 138b. The clamp surfaces 134a, 134b may be configured to face each other when the clamp arms 130a, 130b grip tissue. Features of the clamp arms 130a, 130b and connections between the clamp arms 130a, 130b and the clamp body 128 are described below to be identical. However, it is contemplated that one or more features from the first clamp arm 130a and/or connections of the first clamp arm 130a to the clamp body 128 may be different than features from the second clamp arm 130b and/or connections of the second clamp arm 130b to the clamp body 128. Furthermore, while features of the first clamp arm 130a and connections between the first clamp arm 130a and the clamp body 128 may be described below, it is appreciated that the identical or similar features may be employed with the second clamp arm 130b.

The surgical clamp assembly 126 also includes a linear displacement mechanism 140 coupled to the clamp body 128 and configured to move the clamp arms 130a, 130b. A carrier 142 is coupled to the linear displacement mechanism 140. The carrier 142 is moveable relative to the clamp body 128 along a carrier axis CX in response to movement of the linear displacement mechanism 140. The carrier axis CX may be transverse to the arm axis EX. The carrier 142 is coupled directly to the proximal portions 136a, 136b of each of the clamp arms 130a, 130b. In other words, there are no intermediate linkages connected between the carrier 142 and the clamp arms 130a, 130b. The proximal portions 136a, 136b of the clamp arms 130a, 130b are pivotable relative to the carrier 142 about respective second pivots 144a, 144b in response to movement of the carrier 142. The surgical clamp assembly 126 may comprise biasing members such as springs that bias the distal portions 132a, 132b of the clamp arms 130a, 130b. In some configurations, the distal portions 132a, 132b of the clamp arms 130a, 130b may be biased together. In other configurations, the distal portions 132a, 132b of the clamp arms 130a, 130b may be biased apart.

In many configurations, the tissue being gripped (e.g., a portion of the humerus) may have non-parallel surfaces to be gripped by the clamp arms 130a, 130b. The distal portions 132a, 132b may be formed such that the clamping surfaces 134a, 134b are not parallel to each other to accommodate such non-parallel surfaces. In other configurations, the distal portions 132a, 132b may comprise multiple sections that pivotable relative to each other to clamp a large range of non-parallel surfaces.

In the configurations illustrated in FIGS. 5 and 6, the clamp arms 130a, 130b, the carrier 142, the first pivots 138a, 138b, and the second pivots 144a, 144b are symmetrical across a reference plane that extends through the carrier axis CX. Said differently, the clamp arms 130a, 130b, the carrier 142, the first pivots 138a, 138b, and the second pivots 144a, 144b are symmetrical across the carrier axis CX when viewed from the side as shown in FIGS. 5 and 6. In other configurations, one or more of the clamp arms 130a, 130b, the carrier 142, the first pivots 138a, 138b, and the second pivots 144a, 144b are symmetrical across a reference plane while one or more of the clamp arms 130a, 130b, the carrier 142, the first pivots 138a, 138b, and the second pivots 144a, 144b are not symmetrical across a reference plane. In another configuration, where the clamp arms 130a, 130b, the carrier 142, the first pivots 138a, 138b, and the second pivots 144a, 144b are not each symmetrical across a reference plane, the first clamp arm 130a may still be pivotable relative to the clamp body 128 and the carrier 142 such that the first clamp arm 130a is configured to move in concert with the second clamp arm 130b.

The first pivot 138a may be disposed at a first distance from the carrier axis CX and the second pivot 144a is disposed at a second distance from the carrier axis CX less than the first distance. As described in greater detail below, the second pivot 144a may be configured to be translatable relative to the carrier 142 such that the distance between the second pivot 144a and the carrier axis CX may change based on pivoting of the clamp arm 130a about the first pivot 138a. In some configurations, the first pivot 138a is always closer to the carrier axis CX than the second pivot 144a is to the carrier axis CX in any position of the first clamp arm 130a.

The first and second pivots 138a, 144a may be disposed at a third distance relative to each other greater than the second distance.

The first pivot 138a may be fixed relative to the clamp body 128 and the proximal portion 136a of the clamp arm 130a such that the clamp arm 130a is pivotable relative to the clamp body 128. In other words, the first pivot 138a may comprise a first pivot axis FX that is fixed relative to the clamp body 128 and the proximal portion 136a of the clamp arm 130a may pivot relative to the clamp body 128 about the first pivot axis FX. A first pivot retainer may be disposed at the first pivot 138a to constrain movement between the clamp arm 130a and the clamp body 128. In the illustrated configurations, the first pivot retainer comprises a cylindrical body, e.g., a pin. In other configurations, the first pivot retainer may comprise a partially spherical protrusion. In still other configurations, the first pivot retainer may comprise another shape that is capable of facilitating pivoting of the proximal portion 136a of the clamp arm 130a relative to the clamp body 128 while preventing translation of the proximal portion 136a of the clamp arm 130a from translating relative to the clamp body 128.

Figure 7:
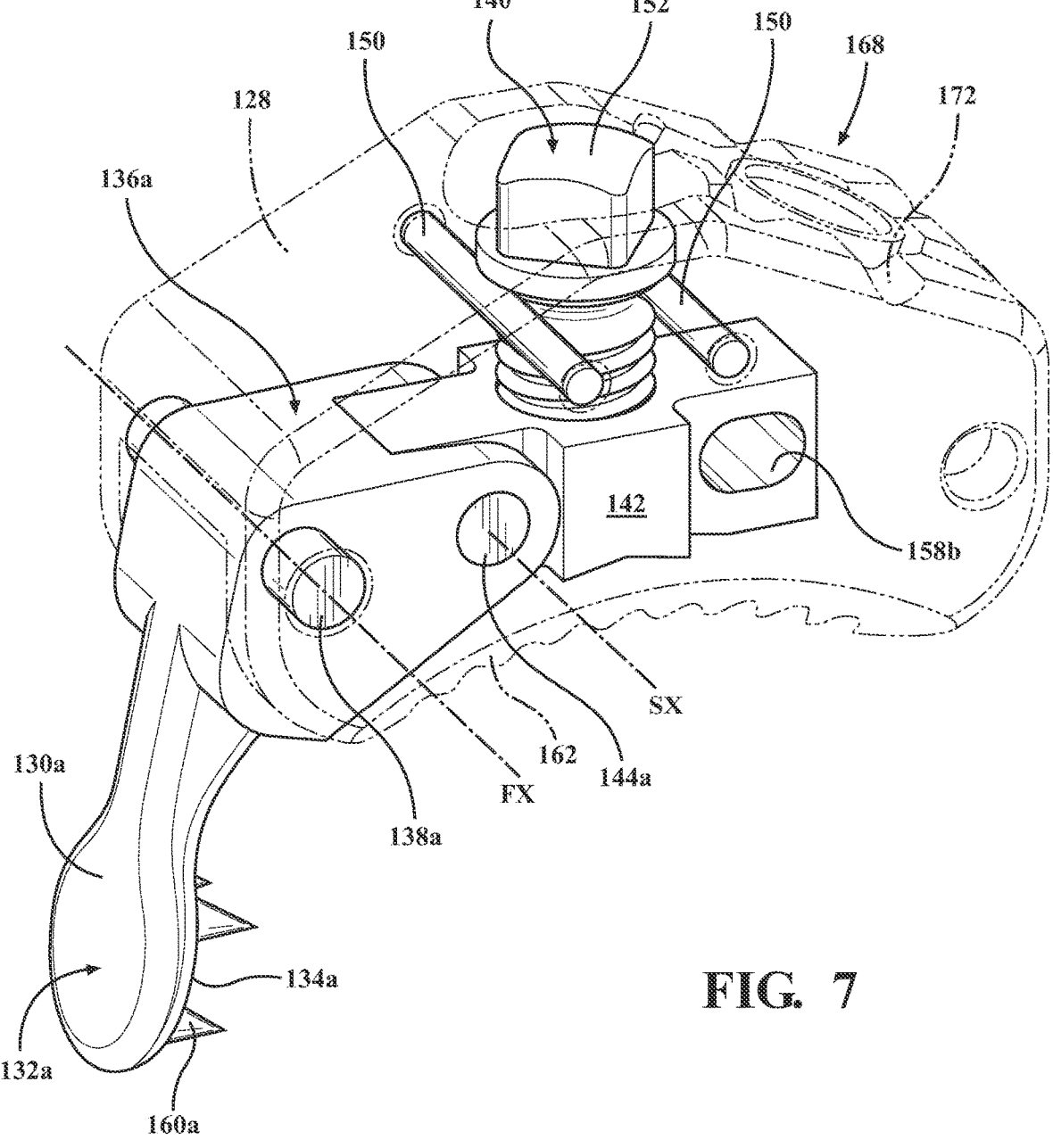
FIG. 7 is a partial perspective view of the surgical clamp assembly of the surgical attachment system of FIG. 1.

As shown in one configuration illustrated in FIGS. 5-7, the linear displacement mechanism 140 may be threadably engageable with a bore 148 of the carrier 142. The linear displacement mechanism 140 may be engageable with the carrier 142 such that the carrier 142 is moveable along the carrier axis CX in response to rotation of the linear displacement mechanism 140. In the illustrated configuration, the linear displacement mechanism 140 comprises a threaded member such as a linearly translatable lead screw. The lead screw 140 may be rotatably coupled to the clamp body 128 and constrained from moving in an axial direction by one or more holders 150 that are coupled to the clamp body 128. The lead screw 140 may be rotatable about a driver axis DX. The driver axis DX may be parallel to the carrier axis CX. In some configurations, the driver axis DX may be colinear with carrier axis CX. In some configurations where the carrier axis CX is used as a reference for relative movement or position and the driver axis DX is colinear with the carrier axis CX, it is contemplated that the same relative movement or position may apply with reference to the driver axis DX.

The linear displacement mechanism 140 may comprise a drive head 152 configured to be rotated by a user for actuating the linear displacement mechanism 140. In one configuration, rotation of the drive head 152 causes movement of the carrier 142 relative to the clamp body 128 and thus, rotation of the proximal portion 136a of the clamp arm 130a relative to the clamp body 128. The drive head 152 may be configured as a square head that can be driven by a corresponding driver bit. However, the drive head 152 may be any suitable size and shape. Furthermore, the driver head 152 can be coupled to a powered hand tool or a non-powered (manually driven) hand tool.

The drive head 152 may be disposed in a bore 154 of the clamp body 128 such that none of the drive head 152 protrudes outside of the clamp body 128. In such a configuration, a cap (not shown) may be removably coupled over the bore 154 to cover the bore 154 and seal the drive head 152 inside the clamp body 128. In other configurations, the linear displacement mechanism 140 may comprise a knob that may be gripped and rotated by a user to effect rotation.

Each holder 150 may comprise a pin or another body configured to axially secure the lead screw to the clamp body 128 while permitting the lead screw 140 to rotate relative to the clamp body 128. As the lead screw 140 is threadably engaged with the carrier 142 and not with the clamp body

128, rotation of the lead screw 140 causes the carrier 142 to move axially relative to the clamp body 128 and the lead screw 140. Axial movement the carrier 142 results in one or both the clamp arms 130a, 130b to pivot relative to the clamp body 128 about the first pivots 138a, 138b. In some configurations, the clamp body 128 may comprise one or both the holders 150.

In other configurations, the relationship between the carrier 142 and the clamp body 128 may be reversed. Specifically, the lead screw 140 may be threadably engageable with the clamp body 128 and the lead screw 140 may be rotatably coupled to the carrier 142 and constrained from moving in an axial direction by one or more holders 150 that are coupled to the carrier 142. Each holder 150 would axially secure the lead screw 140 to the carrier 142 while permitting the lead screw 140 to rotate relative to the carrier 142. As the lead screw 140 is threadably engaged with the clamp body 128 and not with the carrier 142, rotation of the lead screw 140 may cause the carrier 142 to move axially relative to the clamp body 128. In this configuration, the lead screw 140 would move with the carrier 142 relative to the clamp body 128.

In another configuration, a threaded nut (not shown) may be used to move the carrier 142 axially relative to the clamp body 128. In this configuration, the lead screw 140 may be fixed relative to the clamp body 128. The lead screw 140 may extend within a through hole of the carrier 142 and the threaded nut may be threadably engaged with the lead screw 140 such that rotation of the threaded nut causes the threaded nut and the carrier 142 to axially translate relative to the lead screw 140 and the clamp body 128.

In alternative configurations, the linear displacement mechanism 140 may comprise a linear actuator or another device used to provide linear motion of the carrier relative to the clamp body 128 to pivot the first and second clamp arms 130a, 130b.

The second pivot 144a may comprise a second pivot retainer. The second pivot 144a may be fixed relative to the proximal portion 136a of the clamp arm 130a and moveable relative to the carrier 142 such that the second pivot 144a and thus the clamp arm 130a, are pivotable and translatable relative to the carrier 142. The carrier 142 may define a slot 158a to receive the second pivot retainer. The slot 158a may be sized to permit the second pivot retainer to rotate and translate within the slot 158a. In some configurations, the slot 158a is open at one end. The slot 158a may be sized to permit the second pivot retainer to move in a direction that is perpendicular to the carrier axis CX. The carrier 142 may comprise opposing slot walls of the slot 158a that define a height of the slot 158a. The carrier 142 may comprise opposing slot ends defining a width of the slot 158a. The height of the slot 158a may approximate a height of the second pivot retainer such that the second pivot 144a may only translate linearly within the slot 158a. The width of the slot 158a may be greater than the height of the slot 158a. In other configurations the proximal portion 136a of the clamp arm 130a defines the slot 158a and the second pivot 144a is fixed to the carrier 142. Such a configuration would still permit pivoting and translation of the clamp arm 130a relative to the carrier 142.

The clamp arms 130a, 130b may each comprise an arm grip 160a, 160b on the clamp surface 134a, 134b. The clamp body 128 may comprise a body grip 162. The arm grip 160a, 160b and the body grip 162 are configured to grip tissue. The arm grip 160a, 160b and body grip 162 may comprise projections for piercing into and gripping the bone. The projections may be disposed at non-orthogonal angles relative to the surface they project from. The projections may comprise teeth. The teeth may have a conical configuration. However, the projections may have any suitable configuration for gripping the bone.

In other configurations, the arm grip 160a, 160b may be disposed on a floating platform coupled to the clamp arm 130a. The floating platform may be pivotable, swivelable, or otherwise moveably coupled to the clamp arm 130a when not in contact with tissue. When a user operates the linear displacement mechanism to grip the tissue with the clamp arms 130a, 130b, the force acting on the clamp arms 130a, 130b and the tissue may cause the floating platforms to first move to a position that conforms the arm grips 160a, 160b to the tissue and then remain in place.

In other configurations, the arm grip 160a, 160b and the body grip 162 may each have configurations other than teeth configured to fix the clamp assembly 126 to the bone. For example, the arm grip 160a, 160b and the body grip 162 may have an abrasive texture that increases the coefficient of friction between the bone and the arm grip 160a, 160b and the body grip 162 when in contact with the bone. The arm grip 160a, 160b and body grip 162 may have any suitable configuration for fixing the clamp assembly 126 to the bone.

The clamp body 128 may comprise a stationary portion that remains stationary while the clamp arm 130a moves about the first pivot 138a. The stationary portion comprises a distal-facing surface and the body grip 162. The body grip 162 may comprise projections extending distally from the distal-facing surface. The distal-facing surface may be curved to conform to the shape of a humerus. In other configurations, the distal-facing surface may be shaped to conform to the shape of another bone or tissue. The projections and the stationary portion of the clamp body 128 may be monolithic in construction.

In some configurations, a user may first bring the body grip 162 into contact with the tissue to be gripped before operating the linear displacement mechanism 140 to move the clamp arms 130a, 130b toward each other and grip tissue. Specifically, a user may position the body grip against a relatively narrow portion of the humerus below a proximal head portion of the humerus. In other configurations, the user operates the linear displacement mechanism 140 to move the clamp arms 130a, 130b toward each other to grip tissue without first making contact with the body grip 162. Contact of the clamp arms 130a, 130b with the tissue may then bring the body grip 162 into contact with tissue.

The arm grip 160a may be disposed at a fourth distance from the first pivot 138a. The fourth distance may be greater than the third distance. When the fourth distance is greater than the third distance, the distal portion 132a of the clamp arm 130a is configured to pivot about the first pivot 138a at a greater arc length than a given arc length of the second pivot 144a about the first pivot 138a. In other words, the mechanical advantage between the second pivot 144a and the first pivot 138a to the first pivot 138a and the arm grip 160a is less than one. This allows a smaller input by the linear displacement mechanism 144 to result in a larger output (e.g., distance of travel or "throw") of the distal portion 132a of the clamp arm 130a.

The clamp body 128 may define a channel 164 to receive the carrier 142 and permit the carrier 142 to move along the carrier axis CX. The carrier axis CX may be centered in the channel CX. The clamp body 128 may define one or more notches 166a, 166b that further define the channel 164. The notch 166a may be configured to at least partially receive one of the clamp arms 130a to permit the clamp arm 130a to pivot about the first pivot 138a with a greater range.

As shown in FIGS. 3 and 4, the clamp body 128 may comprise a body attachment interface 168 for detachable coupling to the second extension attachment interface 115 of the extension arm 108. The body attachment interface 168 may be oriented transverse to the carrier axis CX. The second extension arm interface 115 may comprise an extension arm rotational adjuster 170. In a similar manner as the tracker rotational adjusters above 118, 120, the extension arm rotational adjuster 170 and the body attachment interface 168 may each comprise lock teeth opposing each other. The lock teeth on the extension arm rotational adjuster 170 and the lock teeth on the body attachment interface 168 may be configured to rotate relative to each other when spaced apart and rotatably lock when in engagement with each other. In the illustrated configuration, the body attachment interface 168 may be configured for kinematic coupling.

The body attachment interface 168 may define recesses 172 that are engaged by complementary projections 174 of the second extension arm interface 115. The recesses may be "V-shaped." The projections 174 of the second extension arm interface 115 and the recesses 172 of the body attachment interface 168 may be configured to rotate relative to each other when spaced apart and rotatably lock when in engagement with each other. The projections 174 may each comprise at least a partially spherical shape. The "V-shape" of the recesses 172 and the partially spherical shape of the projections 174 may provide the kinematic coupling by constraining the six degrees of freedom of movement between the clamp assembly 126 and the second extension attachment interface 115. Specifically, body attachment interface 168 may define six recesses 172. The second extension arm interface 115 may include three projections 174 to interface with three of the six recesses 172. The spacing and number of the projections 174 and recesses 172 permits coupling between the between the clamp assembly 126 and the second extension attachment interface 115 to be coupled in six relative orientations. In other configurations, the number and spacing of projections 174 and recesses 172 may be different to permit more than six orientations or less than six orientations. It is contemplated that kinematic coupling may comprise the opposite configuration. It is also contemplated that kinematic coupling to constrain six degrees of freedom of movement may be achieved in other manners or by using other types of kinematic elements. In another configuration, connection between the extension arm rotational adjuster 170 and the body attachment interface 168 may be configured in any other suitable configuration for kinematic coupling or coupling otherwise the second extension attachment interface 115 to the clamp assembly 126 (e.g., threaded engagement).

The kinematic coupling between the clamp assembly 126 and the second extension attachment interface 115 is particularly useful during surgical applications by offering a repeatable mounting feature. For example, there may be instances during a surgical procedure where separation of the extension attachment interface 115 from the clamp assembly 126 may be necessary to allow movement of the clamped humerus relative to other anatomy without losing the relative position between the clamp assembly 128 and the humerus. In such a situation, the low profile of the clamp assembly 126 without the extension arm 108 or the tracker 54 may be more suitable to not impinge joint movement for surgery and tenting/tension of tissue and surrounding anatomy/surgical environment. The kinematic coupling between the clamp assembly 126 and the second extension attachment interface 115 enables the clamp assembly 126 and the second extension attachment interface 115 to be coupled and decoupled to each other without require re-registration of the tracker 54 to the clamp assembly 126 and/or the humerus.

The clamp assembly 126 described herein has several advantages. The clamp assembly 126 has a large throw size (range of motion) and is sized to fit between the fifth and ninety-fifth percentiles of humerus sizes which provides a wide applicability to surgical procedures without requiring different clamps for different sized patients. The clamp assembly 126 further provides a high clamping force as compared with conventional clamps. The clamp assembly 126 also exhibits a small footprint (i.e., is low profile) in the working area of a surgical site by operating two clamp arms 130a, 130b simultaneously with a single input, which is particularly advantageous for a shoulder replacement surgery where there is limited incision size and surgeon access to the surgical site. This enables the surgical attachment system 106, including the clamp assembly 126, to be utilized in tight spaces and at difficult surgical access angles while providing the ability of the navigation tracker 54 to maintain line-of-sight to the localizer 44. The small footprint of the surgical attachment system 106 further enables unobstructed post joint-reduction range of motion assessment. The clamp assembly 126 also provides the linear displacement mechanism 140 in an ergonomic and user-friendly position thereby reducing the risk of collisions at the surgical site. The clamp assembly 126 may also be affixed to any other type of anatomy or bone. Additionally, the clamp assembly 126 may be affixed on left or right sides of the patient anatomy. Other advantages can be understood from the detailed description and drawings. Other attachment mechanisms have included clamps that secure to the bone.

The above clamping and attachment system can be designed with a configuration, look, or function that differs specifically from the implementation shown in the Figures. The configurations are limited exclusively to the Figures and may include equivalents to any components described herein which operate with a similar function and accomplish a similar result.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency. Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings may be practiced otherwise than as specifically described.

The invention claimed is:

1. A surgical clamp assembly for clamping tissue and supporting a navigation tracker, the surgical clamp assembly comprising:
   a clamp body;
   a first clamp arm coupled to the clamp body;
   a second clamp arm coupled to the clamp body and configured to grip tissue with the first clamp arm, the second clamp arm comprising a distal portion having a clamp surface, and the second clamp arm comprising a proximal portion pivotable relative to the clamp body about a first pivot;

a linear displacement mechanism coupled to the clamp body; and a carrier coupled to the linear displacement mechanism, the carrier being moveable relative to the clamp body along a carrier axis in response to movement of the linear displacement mechanism, and the carrier being coupled directly to the proximal portion of the second clamp arm;

wherein the proximal portion of the second clamp arm is pivotable relative to the carrier about a second pivot in response to movement of the carrier, and wherein the second pivot is fixed relative to the proximal portion of the second clamp arm and moveable relative to the carrier.

2. The surgical clamp assembly of claim 1, wherein the first pivot is fixed relative to the clamp body and the proximal portion of the second clamp arm such that the second clamp arm is pivotable relative to the clamp body.

3. The surgical clamp assembly of claim 1, further comprising a retainer disposed at the second pivot, and the retainer being coupled to the proximal portion of the second clamp arm and the carrier, wherein the carrier defines a slot to receive the retainer.

4. The surgical clamp assembly of claim 3, wherein the carrier comprises opposing slot walls of the slot that defines a height of the slot, and wherein the carrier comprises opposing slot ends defining a width of the slot, and wherein the height of the slot approximates a height of the retainer.

5. The surgical clamp assembly of claim 1, wherein the second clamp arm comprises an arm grip on the clamp surface, and wherein the clamp body comprises a body grip, the arm grip and the body grip are configured to grip tissue.

6. The surgical clamp assembly of claim 1, wherein the clamp body comprises a stationary portion that remains stationary while the second clamp arm moves about the first pivot, the stationary portion comprising a distal-facing surface and a grip extending distally from the distal-facing surface.

7. The surgical clamp assembly of claim 1, wherein the linear displacement mechanism is engageable with the carrier such that the carrier is moveable along the carrier axis in response to rotation of the linear displacement mechanism.

8. The surgical clamp assembly of claim 7, wherein the linear displacement mechanism is threadably engageable with the carrier.

9. The surgical clamp assembly of claim 1, wherein the clamp body defines a channel to receive the carrier and permit the carrier to move along the carrier axis.

10. The surgical clamp assembly of claim 9, wherein the carrier axis is centered in the channel.

11. The surgical clamp assembly of claim 9, wherein the clamp body defines a notch further defining the channel, the notch configured to at least partially receive the second clamp arm to permit the second clamp arm to pivot about the first pivot with a greater range.

12. The surgical clamp assembly of claim 1, wherein the clamp body comprises an attachment interface for detachable coupling to an extension arm.

13. The surgical clamp assembly of claim 1, wherein the first pivot is disposed at a first distance from the carrier axis and the second pivot is disposed at a second distance from the carrier axis less than the first distance.

14. The surgical clamp assembly of claim 1, wherein the first clamp arm is pivotable relative to the clamp body and the carrier and configured to move in concert with the second clamp arm.

15. The surgical clamp assembly of claim 1, wherein the first clamp arm is symmetrical of the second clamp arm about a reference plane extending through the carrier axis.

16. A surgical attachment system for fixing a navigation tracker to a portion of bone, the surgical attachment system comprising:

an extension arm configured to support the navigation tracker; and a surgical clamp assembly configured to support the extension arm and comprising:

a clamp body, a first clamp arm coupled to the clamp body, a second clamp arm coupled to the clamp body and configured to grip tissue with the first clamp arm, the second clamp arm comprising a distal portion having a clamp surface, and the second clamp arm comprising a proximal portion pivotable relative to the clamp body about a first pivot, a linear displacement mechanism coupled to the clamp body, and a carrier coupled to the linear displacement mechanism, the carrier being moveable relative to the clamp body along a carrier axis in response to movement of the linear displacement mechanism, and the carrier being coupled directly to the proximal portion of the second clamp arm;

wherein the proximal portion of the second clamp arm is pivotable relative to the carrier about a second pivot in response to movement of the carrier, and wherein the second pivot is fixed relative to the proximal portion of the second clamp arm and moveable relative to the carrier.

17. The surgical attachment system of claim 16, further comprising an extension arm rotational adjuster configured to selectively rotate the extension arm relative to the clamp body about an arm axis.

18. The surgical attachment system of claim 17, wherein the arm axis is transverse to the carrier axis.

19. A surgical tracking system comprising:

a navigation tracker; and a surgical attachment system for fixing the navigation tracker to a portion of bone, the surgical attachment system comprising:

an extension arm configured to support the navigation tracker, and a surgical clamp assembly configured to support the extension arm and comprising:

a clamp body, a first clamp arm, a second clamp arm coupled to the clamp body and configured to grip tissue with the first clamp arm, the second clamp arm comprising a distal portion having a clamp surface, and the second clamp arm comprising a proximal portion pivotable relative to the clamp body about a first pivot, a linear displacement mechanism coupled to the clamp body, and a carrier coupled to the linear displacement mechanism, the carrier being moveable relative to the clamp body along a carrier axis in response to movement of the linear displacement mechanism, and the carrier being coupled directly to the proximal portion of the second clamp arm, wherein the proximal portion of the second clamp arm is pivotable relative to the carrier about a respective second pivot in response to movement of the carrier, and wherein the second pivot is fixed relative to the proximal portion of the second clamp arm and moveable relative to the carrier.

\* \* \* \* \*